US011661417B2

(12) United States Patent
Pan et al.

(10) Patent No.: US 11,661,417 B2
(45) Date of Patent: May 30, 2023

(54) LOW-MOLECULAR MASS ORGANIC GELLANT AND PREPARATION METHOD AND USE THEREOF

(71) Applicant: Tianjin University, Tianjin (CN)

(72) Inventors: Lun Pan, Tianjin (CN); Jijun Zou, Tianjin (CN); Yang Liu, Tianjin (CN); Xiangwen Zhang, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 17/855,574

(22) Filed: Jun. 30, 2022

(65) Prior Publication Data

US 2023/0061028 A1   Mar. 2, 2023

(30) Foreign Application Priority Data

Aug. 17, 2021  (CN) .......................... 202110942442.8

(51) Int. Cl.
| | | |
|---|---|---|
| *C07D 317/08* | (2006.01) | |
| *C07D 407/06* | (2006.01) | |
| *C10L 5/40* | (2006.01) | |

(52) U.S. Cl.
CPC ......... *C07D 407/06* (2013.01); *C07D 317/08* (2013.01); *C10L 5/40* (2013.01)

(58) Field of Classification Search
CPC ........................... C07D 407/06; C07D 317/08
See application file for complete search history.

(56) References Cited

U.S. PATENT DOCUMENTS

| | | | | |
|---|---|---|---|---|
| 8,741,044 B1 * | 6/2014 | Chopra | ................... | C09D 11/38 |
| | | | | 106/31.29 |
| 10,343,144 B2 * | 7/2019 | Ravishankar | ........ | B01J 20/3425 |
| 10,894,781 B2 * | 1/2021 | Ravishankar | ........ | C07D 317/20 |

FOREIGN PATENT DOCUMENTS

WO    WO-2006009353 A1 *  1/2006  ............... C07H 3/08

OTHER PUBLICATIONS

Padwal, Manisha et al.; "Gel propellants" Progress in Energy and Combustion Science; vol. 83; Mar. 2021; https://doi.org/10.1016/j.pecs.2020.100885.

(Continued)

*Primary Examiner* — Ellen M McAvoy
*Assistant Examiner* — Ming Cheung Po
(74) *Attorney, Agent, or Firm* — Thorpe North and Western, LLP; David W. Osborne

(57) ABSTRACT

The present disclosure provides a low-molecular mass organic gellant and a preparation method and use thereof, belonging to the technical field of gelled fuels. The low-molecular mass organic gellant has a cyclopropane structure. The cyclopropane structure belongs to a high-tension structure, which endows the gellant with excellent gel properties; in addition, the high-tension cyclopropane structure is also capable of greatly improving a combustion performance of the gellant, shortening an ignition delay time of the fuel, and promoting combustion. Moreover, multiple hydroxyl groups contained in the low-molecular mass organic gellant is capable of effectively forming a gel through hydrogen bonding; therefore, the gellant has excellent gel and shear thinning properties for high-energy density fuel and energetic nanofluid fuel, with a critical gellant concentration of not greater than 1% when forming a stable gel.

6 Claims, 2 Drawing Sheets

(56) References Cited

OTHER PUBLICATIONS

Lee, Donggi et al.; "Autoignition Behavior of an Ethanol-Methylcellulose Gel Droplet in a Hot Environment" *Energies* 2018, 11, 2168. https://doi.org/10.3390/en11082168; Aug. 19, 2018; 11 pages.

* cited by examiner

LOW-MOLECULAR MASS ORGANIC GELLANT AND PREPARATION METHOD AND USE THEREOF

CROSS REFERENCE TO RELATED APPLICATION

This patent application claims the benefit and priority of Chinese Patent Application No. 202110942442.8, filed on Aug. 17, 2021, the disclosure of which is incorporated by reference herein in its entirety as part of the present application.

TECHNICAL FIELD

The present disclosure relates to the technical field of gelled fuels, in particular to a low-molecular mass organic gallant, related compositions, and preparation methods and uses thereof.

BACKGROUND ART

To meet the needs of aerospace, fuel that provides power must have desirable combustibility and excellent usability. Fuel in a gelled form or state (i.e. "gelled fuel" typically maintains a stable gel state during storage and transportation, and can be transformed into a low-viscosity liquid state after being subjected to external shearing during use. Therefore, gelled fuel has the advantages of both solid fuel and liquid fuel, and can effectively improve the fuel's usability. On this basis, an energy density of the fuel can be greatly improved by adding energetic metal nanoparticles (such as aluminum and boron) to the gel, and a storage stability of the fuel can be improved by a gel state, thereby greatly improving overall fuel performance.

Although a structure of the gelled fuel can be destroyed by external force to obtain liquid fuel, the viscosity of gelled fuel may increase relative to that of the liquid fuel due to a certain inherent recovery capability of the gel, making it more difficult to atomize. Moreover, differences in the combustion performance between gellant and fuel may also affect the use of gelled fuel. Therefore, an important way to reduce the influence of gellant on fuel is to reduce a content of the gellant. At present, the reported gellants can be divided into organic gellants and inorganic gellants, where the organic gellants can be further divided into polymer-based gellants and low-molecular mass organic gellants. When forming a stable gel, inorganic gellants and the polymer-based gellants are required amounts of generally not less (e.g. more or greater) than 5 wt %, and inorganic gellant is not flammable. This has a great influence on the combustion performance of fuel. On the contrary, low-molecular mass organic gellants are not only flammable, but also have a critical gellant concentration not greater (e.g. less) than 1 wt %; meanwhile, gelled fuel using the low-molecular mass organic gellant has a desirable shear thinning performance to maintain an inherent property of the fuel to the greatest extent (Padwal M B, Natan B, Mishra D P. Gel propellants [J]. *Progress in Energy and Combustion Science*, 2021, 83: 100885).

There are four stages in the combustion of organogel droplets due to differences in the combustion performance between gellants and liquid fuels. A first stage is a heating stage, which is similar to the combustion of pure liquid fuel droplets; in a second stage, the gellant may form a gel layer on a surface of the droplet, and expand or micro-explode as fuel inside the droplet is heated; in a third stage, rupture of the gel layer initiates fuel vapor injection and combustion; and in a fourth stage, the gel layer burns (Lee D, Won J, Baek S W, et al. Autoignition Behavior of an Ethanol-Methylcellulose Gel Droplet in a Hot Environment [J]. *Energies*, 2018, 11 (8)). This indicates that a combustion rate of the gelled fuel is reduced compared to that of a liquid fuel. Therefore, improving the combustion rate of a gelled fuel is of great significance for use of gelled fuel. Without changing an inherent structure of the fuel, one of the most feasible methods to improve a gelled fuel's combustion rate is by changing the structure of the gellant in ways that enhance combustion performance. Therefore, flammable and low-molecular mass organic gellants with a high energy-containing structure, that can simultaneously realize gel properties and combustion-promoting effects, and thus improve the comprehensive properties of a gelled fuel continue to be sought.

SUMMARY

An objective of the present disclosure is to provide low-molecular mass organic gellants, compositions, and preparation methods and uses thereof. The low-molecular mass organic gellant has a high-tension structure, gel properties, and combustion-promoting effects.

To achieve the above objective, the present disclosure provides the following exemplary technical solutions.

In one embodiment, the present disclosure provides a low-molecular mass organic gellant, having a structure shown in formula I:

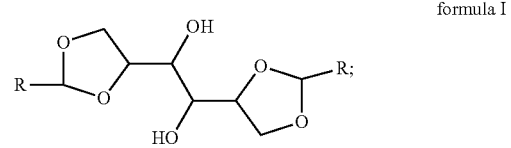

formula I where
R is selected from the group consisting of

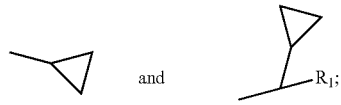

and $R_1$ is selected from the group consisting of —H, —$CH_3$, —$CH_2CH_3$, and Cl.

In another embodiment, the low-molecular mass organic gellant may be selected from the group consisting of:

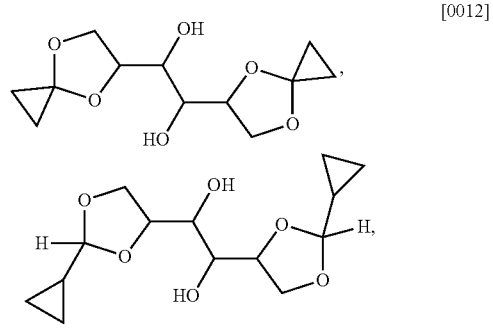

[0012]

-continued

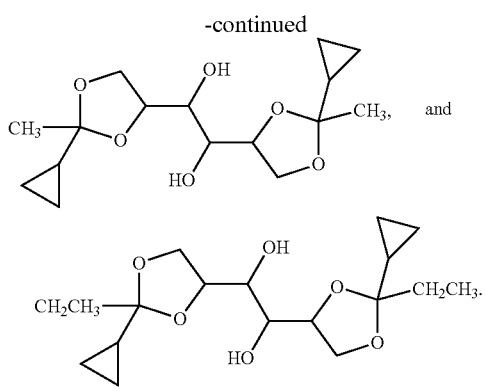

The present disclosure further provides a preparation method of the low-molecular mass organic gellant, including the following steps:

mixing D-mannitol, a high-tension structure-containing compound, a catalyst, and an organic solvent to conduct condensation to obtain the low-molecular mass organic gellant; where the high-tension structure-containing compound has a structure shown in formula II or formula III:

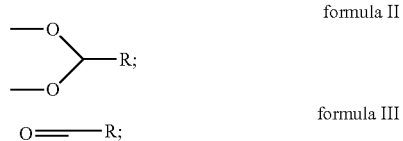

formula II formula III

R is selected from the group consisting of

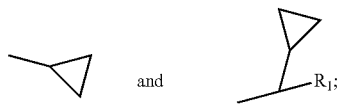

and $R_1$ is selected from the group consisting of —H, —$CH_3$, —$CH_2CH_3$, and Cl.

In one embodiment, the D-mannitol and the high-tension structure-containing compound may have a molar ratio of 1:(2.0-3.5).

In one embodiment, the catalyst may be selected from the group consisting of zinc chloride and p-toluenesulfonic acid.

In one embodiment, the zinc chloride and the D-mannitol may have a molar ratio of (0.03-0.06):0.05; and the p-toluenesulfonic acid and the D-mannitol may have a molar ratio of (0.01-0.03):0.05.

In one embodiment, the condensation may be conducted at 20° C. to 60° C. for 12 h to 48 h.

In one embodiment, the organic solvent may be selected from the group consisting of dimethylformamide and 1,2-dimethoxyethane.

The present disclosure further provides use of the low-molecular mass organic gellant or a low-molecular mass organic gellant prepared by the preparation methods in gelled fuel.

In one embodiment, the gelled fuel may include liquid jet fuel, high-energy density fuel or energetic nanofluid fuel.

The present disclosure provides a low-molecular mass organic gellant. The low-molecular mass organic gellant includes a cyclopropane structure; the cyclopropane structure is a high-tension structure, where a bond angle is in a twisted state and has a certain amount of tension energy, resulting in an extremely unstable structure. Therefore, the structure is more flammable, can improve a combustion performance of the gellant, shorten an ignition delay time of the fuel, and promote combustion. Moreover, multiple hydroxyl groups contained in the low-molecular mass organic gellant is capable of effectively forming a gel through hydrogen bonding and endowing the gellant with excellent gel properties; therefore, the gellant has excellent gel and shear thinning properties for high-energy density fuel and energetic nanofluid fuel, with a critical gellant concentration of not greater than 1% when forming a stable gel.

The present disclosure further provides preparation methods of the low-molecular mass organic gellant. In one embodiment, D-mannitol is used as a starting material, a cyclopropane structure is introduced through hydroxyl protection, to form the low-molecular mass organic gellant that has effective gel properties for fuel and plays a role in promoting combustion. Such a preparation method has a simple preparation process, wide source of raw materials, and low cost.

In the present disclosure, the low-molecular mass organic gellant can prepare 3 # jet fuel (RP-3), high-density fuel (such as HD-01, HD-3, and QC), and energetic nanofluid fuel into gelled fuels with an excellent gel performance, to further prepare gelled fuels with shear thinning properties while significantly reducing the ignition delay time. The gellant is suitable for the gelation of liquid jet fuel, high-energy density fuel, and energetic nanofluid fuel, with an effectively-improved combustion rate of the gelled fuel.

The results of examples show that the low-molecular mass organic gellant can effectively gel (e.g. gelate) various high-density fuels, with a minimum gel-forming concentration not higher than (i.e. less than) 1 wt % of a total weight or mass of the gel; in addition, the formed gel has excellent shear thinning and thixotropic properties, and has an obvious combustion-promoting effect compared with the gellant that is free of a cyclopropane structure.

DETAILED DESCRIPTION OF THE EMBODIMENTS

Figure 1:
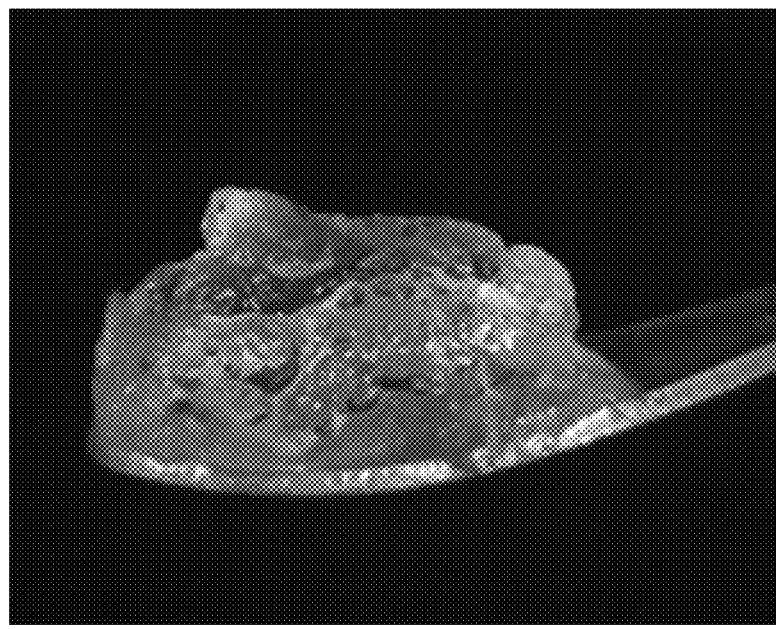
FIG. 1 shows a physical picture of JP-10 gelled fuel prepared in Use Example 1.

The present disclosure provides low-molecular mass organic gellants, having a structure shown in formula I:

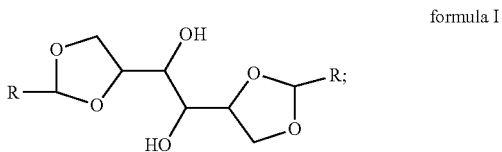

formula I where

R is selected from the group consisting of

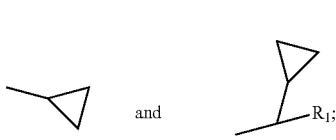

and $R_1$ is selected from the group consisting of —H, —$CH_3$, —$CH_2CH_3$, and Cl.

In the disclosure, the low-molecular mass organic gellant is can be selected from the group consisting of:

[0036]

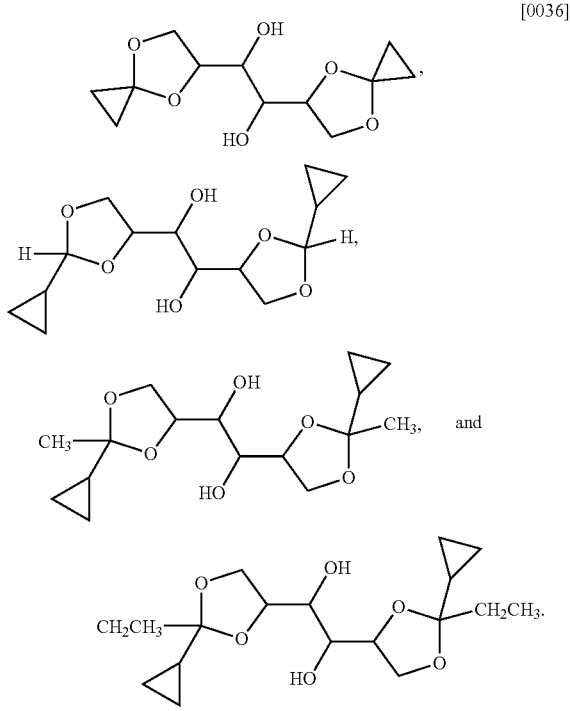

The present disclosure further provides preparation methods of the low-molecular mass organic gellant, including the following steps:

mixing D-mannitol, a high tension structure-containing compound, a catalyst, and an organic solvent to conduct condensation to obtain the low-molecular mass organic gellant; where the high tension structure-containing compound has a structure shown in formula II or formula III:

formula II

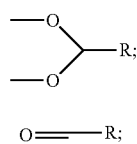

formula III

R is selected from the group consisting of

and $R_1$ is selected from the group consisting of —H, —$CH_3$, —$CH_2CH_3$, and Cl.

In the present disclosure, unless otherwise specified, all raw materials required for preparation are commercially available products well known to persons skilled in the art.

In the present disclosure, the D-mannitol, the high-tension structure-containing compound, the catalyst, and the organic solvent are mixed to conduct condensation. The high tension structure-containing compound can be selected from the group consisting of cycloacetone, cyclopropanecarboxaldehyde, cyclopropyl methyl ketone, cyclopropyl ethyl ketone, (1,1-dimethoxy)methylcyclopropane, (1,1-dimethoxy)ethylcyclopropane, and cyclopropylcarbonyl chloride; and the D-mannitol and the high tension structure-containing compound have a molar ratio of 1:(2.0-3.5), more specifically 1:(2.8-3.2).

In the present disclosure, the catalyst can be selected from the group consisting of zinc chloride and p-toluenesulfonic acid; the zinc chloride and the D-mannitol have a molar ratio of (0.03-0.06):0.05, more specifically 0.05:0.05; and the p-toluenesulfonic acid and the D-mannitol have a molar ratio of (0.01-0.03):0.05, more specifically 0.02:0.05.

In the present disclosure, the organic solvent can be selected from the group consisting of dimethylformamide and 1,2-dimethoxyethane; and the D-mannitol and the organic solvent have an amount ratio of 0.05 mol:(100-150) mL, more specifically 0.05 mol:(110-130) mL.

In the present disclosure, the D-mannitol, the high-tension structure-containing compound, the catalyst, and the organic solvent can be mixed or otherwise combined by: dissolving the D-mannitol and the catalyst in the organic solvent, and adding the high-tension structure-containing compound.

In the present disclosure, the condensation can be conducted at from about 20° C. to about 60° C., and in some cases from about 30° C. to about 50° C. for a time of from about 12 h to about 48 h, and in some embodiments for a time of about 36 h; the condensation can be conducted by stirring; there is no special limitation on a speed of the stirring, which can be conducted according to a process well known in the art.

In the present disclosure, the condensation is shown in the following formula (where R is the same as described above):

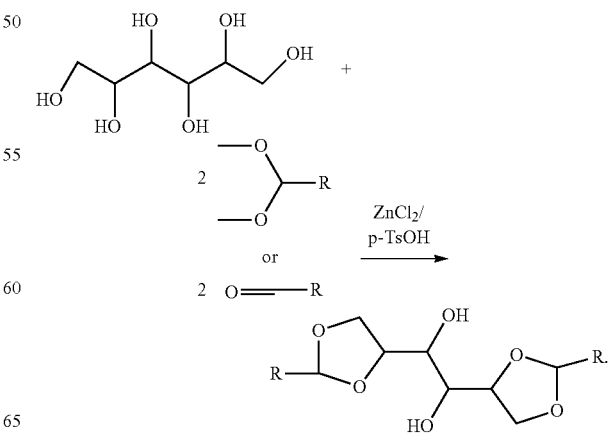

After the condensation, an obtained product system can be mixed with a saturated sodium chloride solution and dichloromethane (the saturated sodium chloride solution and the dichloromethane have a volume ratio of 1:1), and stirred for 15 min; a resulting material is filtered and washed with the dichloromethane; an obtained washing material is extracted with the dichloromethane to remove an aqueous phase, and organic phases are combined; the organic phase is washed with a saturated NaCl solution, dried with anhydrous $Na_2SO_4$, filtered, and rotary-evaporated to obtain the low-molecular mass organic gellant. There is no special limitation on processes of the filtration, washing, extraction and rotary evaporation, and the processes can be conducted according to those well-known in the art.

The present disclosure further provides use of the low-molecular mass organic gellant or a low-molecular mass organic gellant prepared by the preparation method in gelled fuel. The gelled fuel includes liquid jet fuel, high-energy density fuel or energetic nanofluid fuel. In a use example, the gelled fuel includes specifically JP-10 fuel, RP-3 fuel, HD-03 fuel, QC fuel, or aluminum-based energetic nanofluid (5% Al+HD-01).

In the present disclosure, there is no special limitation on a method of the use, and methods well known in the art can be used. In a use example, a preparation method of the gelled fuel specifically includes: mixing the low-molecular mass organic gellant with the fuel, heating and stirring until a resulting mixture becomes clear; the mixture is cooled at room temperature until a non-flowing solid-like substance is obtained, thereby forming the gelled fuel. There is no special limitation on a process of the heating and stirring, which can be adjusted according to actual needs.

The technical solutions in the present disclosure are clearly and completely described below in conjunction with examples of the present disclosure. It is clear that the described examples are merely a part, rather than all of the examples of the present disclosure. All other examples obtained by a person of ordinary skill in the art based on the examples of the present disclosure without creative efforts shall fall within the protection scope of the present disclosure.

Example 1

9.11 g of D-mannitol (0.05 mol) and 6.82 g of zinc chloride (0.05 mol) were dissolved in 100 mL of DMF, 8.41 g of cycloacetone (0.15 mol) was added, and a reaction was conducted by stirring at 25° C. for 12 h; 100 mL of a saturated sodium chloride solution and 100 mL of dichloromethane were added to an obtained system, and stirred for 15 min; an obtained material was filtered and washed with 100 mL of the dichloromethane, an obtained product was extracted with the dichloromethane to remove an aqueous phase, organic phases were combined and washed with the saturated NaCl solution; and an obtained washed material was dried with anhydrous $Na_2SO_4$. A dried material was filtered and subjected to rotary evaporation to obtain 5.1 g of a low-molecular mass organic gellant with a structural formula of:

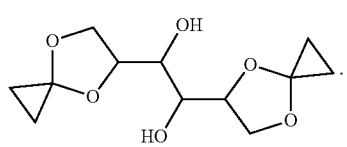 [SMILES: OC(C1COC2(CC2)O1)C(O)C1COC2(CC2)O1]

Example 2

9.11 g of D-mannitol (0.05 mol) and 6.82 g of zinc chloride (0.05 mol) were dissolved in 100 mL of DMF, 10.51 g of cyclopropanecarboxaldehyde (0.15 mol) was added, and a reaction was conducted by stirring at 25° C. for 12 h; 100 mL of a saturated sodium chloride solution and 100 mL of dichloromethane were added to an obtained system, and stirred for 15 min; an obtained material was filtered and washed with 100 mL of the dichloromethane, an obtained product was extracted with the dichloromethane to remove an aqueous phase, organic phases were combined and washed with the saturated NaCl solution; and an obtained washed material was dried with anhydrous $Na_2SO_4$. A dried material was filtered and subjected to rotary evaporation to obtain 6.0 g of a low-molecular mass organic gellant with a structural formula of:

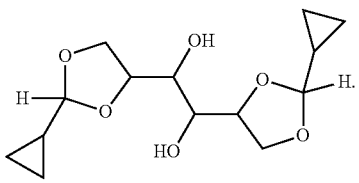

Example 3

9.11 g of D-mannitol (0.05 mol) and 6.82 g of zinc chloride (0.05 mol) were dissolved in 100 mL of DMF, 12.62 g of cyclopropyl methyl ketone (0.15 mol) was added, and a reaction was conducted by stirring at 30° C. for 20 h; 100 mL of a saturated sodium chloride solution and 100 mL of dichloromethane were added to an obtained system, and stirred for 15 min; an obtained material was filtered and washed with 100 mL of the dichloromethane, an obtained product was extracted with the dichloromethane to remove an aqueous phase, organic phases were combined and washed with the saturated NaCl solution; and an obtained washed material was dried with anhydrous $Na_2SO_4$. A dried material was filtered and subjected to rotary evaporation to obtain 6.3 g of a low-molecular mass organic gellant with a structural formula of:

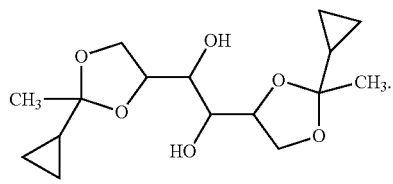 [SMILES: CC1(C2CC2)OCC(C(O)C(O)C2COC(C)(C3CC3)O2)O1]

Example 4

9.11 g of D-mannitol (0.05 mol) and 1.88 g of p-toluenesulfonic acid (0.01 mol) were dissolved in 100 mL of DMF, 17.42 g of (1,1-dimethoxy)methylcyclopropane (0.15 mol) was added, and a reaction was conducted by stirring at 40° C. for 36 h; 100 mL of a saturated sodium chloride solution and 100 mL of dichloromethane were added to an obtained system, and stirred for 15 min; an obtained material was filtered and washed with 100 mL of the dichloromethane, an obtained product was extracted with the dichloromethane to remove an aqueous phase, organic phases were combined and washed with the saturated NaCl solution; and an obtained washed material was dried with anhydrous $Na_2SO_4$. A dried material was filtered and subjected to rotary evaporation to obtain 9.6 g of a low-molecular mass organic gellant with a structural formula the same as that of Example 2.

Example 5

9.11 g of D-mannitol (0.05 mol) and 1.88 g of p-toluenesulfonic acid (0.01 mol) were dissolved in 100 mL of DMF, 19.68 g of (1,1-dimethoxy)ethylcyclopropane (0.15 mol) was added, and a reaction was conducted by stirring at 40° C. for 48 h; 100 mL of a saturated sodium chloride solution and 100 mL of dichloromethane were added to an obtained system, and stirred for 15 min; an obtained material was filtered and washed with 100 mL of the dichloromethane, an obtained product was extracted with the dichloromethane to remove an aqueous phase, organic phases were combined and washed with the saturated NaCl solution; and an obtained washed material was dried with anhydrous $Na_2SO_4$. A dried material was filtered and subjected to rotary evaporation to obtain 12.5 g of a low-molecular mass organic gellant with a structural formula the same as that of Example 3.

Comparative Example 1

This example was different from Example 1 in that the cycloacetone was replaced with acetone of an equivalent amount, others were the same as those in Example 1.

Comparative Example 2

This example was different from Example 2 in that the cyclopropanecarboxaldehyde was replaced with 2-methylpropanal of an equivalent amount, others were the same as those in Example 2.

Comparative Example 3

This example was different from Example 3 in that the cyclopropyl methyl ketone was replaced with 3-methyl-2-butanone of an equivalent amount, others were the same as those in Example 3.

Comparative Example 4

This example was different from Example 4 in that the (1,1-dimethoxy)methylcyclopropane was replaced with 2-methylpropanal of an equivalent amount, others were the same as those in Example 4.

Comparative Example 5

This example was different from Example 5 in that the (1,1-dimethoxy)ethylcyclopropane was replaced with 3-methyl-2-butanone of an equivalent amount, others were the same as those in Example 5.

Use Example 1

The gellant prepared in Example 1 was mixed with JP-10 fuel in a mass ratio of 1/99, and heated by stirring at 90° C. until a solution became clear; the solution was cooled at room temperature for 1 h to a non-flowing solid-like state to form gelled fuel, which was a translucent gelled fuel.

1) The gelled fuel prepared in Use Example 1 was destroyed by stirring with an external force, and allowed to stand for 5 h to 10 h; it was observed that the gelled fuel could be restored to a gel state, indicating that the prepared gelled fuel had recoagulation properties.

2) A viscosity of the prepared gelled fuel was tested by a rotational viscometer. The gelled fuel had a viscosity of 467.5 Pa s, and a viscosity decreased to 97 mPa s after shearing at 60 rpm for 10 min.

Comparative Use Example 1

The only difference from Use Example 1 was that the gellant of Example 1 was replaced with the gellant of Comparative Example 1, and others were the same as Use Example 1.

The ignition delay time of the gelled fuels prepared in Use Example 1 and Comparative Use Example 1 was measured by a flat plate ignition test. The results show that under 1 wt % of the gellant, the ignition delay time of the JP-10 gelled fuel prepared in Use Example 1 at 430° C. is 2378 ms, which is shortened by 496 ms compared with the gelled fuel prepared with diacetone-D-mannitol as a gellant in Comparative Use Example 1.

Use Example 2

The gellant prepared in Example 2 was mixed with RP-3 fuel in a mass ratio of 1/99, and heated by stirring at 100° C. until a solution became clear; the solution was cooled at room temperature to a non-flowing solid-like state to form gelled fuel, which was a translucent gelled fuel.

According to the method of Use Example 1, the gelled fuel of Use Example 2 was tested. The results show that the gelled fuel has recoagulation properties; after being destroyed by stirring with external force, the gelled fuel can be restored to a gel state after standing for 5 h to 10 h. The gelled fuel has a viscosity of 417.5 Pa s, and a viscosity decreased to 85 mPa s after shearing at 60 rpm.

Comparative Use Example 2

The only difference from Use Example 2 was that the gellant of Example 2 was replaced with the gellant of Comparative Example 2, and others were the same as Use Example 2.

The ignition delay time of the gelled fuels prepared in Use Example 2 and Comparative Use Example 2 was measured by the flat plate ignition test. The results show that under 1 wt % of the gellant, the ignition delay time of the RP-3 gelled fuel at 420° C. is 2012 ms. Compared with the gelled fuel prepared in Comparative Use Example 2, the ignition delay time is shortened by 422 ms.

Use Example 3

The gellant prepared in Example 3 was mixed with HD-03 fuel a mass ratio of 1/99, and heated by stirring at 110° C. until a solution became clear; the solution was cooled at room temperature to a non-flowing solid-like state to form gelled fuel, which was a translucent gelled fuel.

According to the method of Use Example 1, the gelled fuel of Use Example 3 was tested. The results show that the gelled fuel has recoagulation properties; after being destroyed by stirring with external force, the gelled fuel can be restored to a gel state after standing for 5 h to 10 h. The gelled fuel has a viscosity of 1081.7 Pa s, and a viscosity decreased to 219 mPa s after shearing at 60 rpm for 10 min.

Comparative Use Example 3

The only difference from Use Example 3 was that the gellant of Example 3 was replaced with the gellant of Comparative Example 3, and others were the same as Use Example 3.

The ignition delay time of the gelled fuels prepared in Use Example 3 and Comparative Use Example 3 measured by the flat plate ignition test. The results show that under 1 wt % of the gellant, the ignition delay time of the HD-03 gelled fuel at 440° C. is 2767 ms. Compared with the gelled fuel prepared in Comparative Use Example 3, the ignition delay time is shortened by 361 ms.

Use Example 4

The gellant prepared in Example 4 was mixed with QC fuel in a mass ratio of 1/99, and heated by stirring at 80° C. until a solution became clear; the solution was cooled at room temperature to a non-flowing solid-like state to form gelled fuel, which was a translucent gelled fuel.

According to the method of Use Example 1, the gelled fuel of Use Example 4 was tested. The results show that the gelled fuel has recoagulation properties; after being destroyed by stirring with external force, the gelled fuel can be restored to a gel state after standing for 5 h to 10 h. The gelled fuel has a viscosity of 1599.1 Pa s, and a viscosity decreased to 155 mPa s after shearing at 60 rpm for 10 min.

Comparative Use Example 4

The only difference from Use Example 4 was that the gellant of Example 4 was replaced with the gellant of Comparative Example 4, and others were the same as Use Example 4.

The ignition delay time of the gelled fuels prepared in Use Example 4 and Comparative Use Example 4 measured by the flat plate ignition test. The results show that under 1 wt % of the gellant, the ignition delay time of the QC gelled fuel at 460° C. is 3054 ms. Compared with the gelled fuel prepared in Comparative Use Example 4, the ignition delay time is shortened by 422 ms.

Use Example 5

The gellant prepared in Example 5 was mixed with aluminum-based energetic nanofluid (5% Al+HD-01) in a mass ratio of 1/99, and heated by stirring at 100° C. until a solution became clear; the solution was cooled at room temperature to a non-flowing solid-like state to form gelled fuel.

According to the method of Use Example 1, the gelled fuel of Use Example 5 was tested. The results show that the gelled fuel has recoagulation properties; after being destroyed by stirring with external force, the gelled fuel can be restored to a gel state after standing for 5 h to 10 h. The gelled fuel has a viscosity of 1276.1 Pa s, and a viscosity decreased to 135 mPa s after shearing at 60 rpm for 10 min.

Comparative Use Example 5

The only difference from Use Example 5 was that the gellant of Example 5 was replaced with the gellant of Comparative Example 5, and others were the same as Use Example 5.

The ignition delay time of the gelled fuels prepared in Use Example 5 and Comparative Use Example 5 was measured by a flat plate ignition test. The results show that under 1 wt % of the gellant, the ignition delay time of the aluminum-based energetic nanofluid (5% Al+HD-01) at 430° C. is 2233 ms, which is shortened by 323 ms compared with the gelled fuel prepared in Comparative Use Example 5.

Characterization and Performance Test 1) a picture of the gelled fuel prepared in Use Example 1 was taken, and an actual picture obtained was shown in FIG. 1; it can be seen from FIG. 1 that the gelled fuel is translucent and has a desirable gel state.

Figure 2:
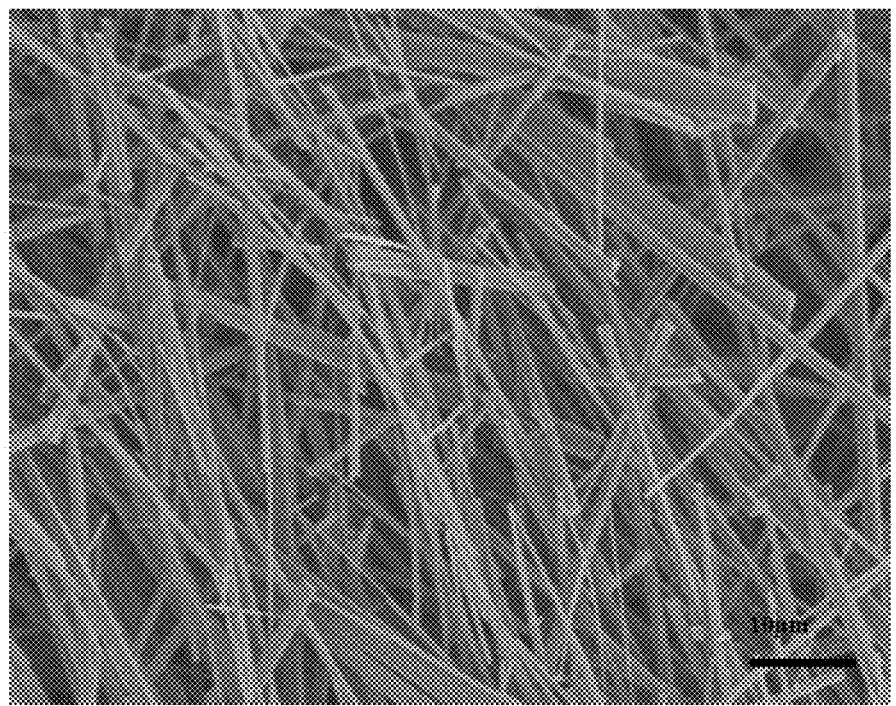
FIG. 2 shows a scanning electron microscope (SEM) image of the JP-10 gelled fuel prepared in Use Example 1.

2) A SEM test was conducted on the gelled fuel prepared in Use Example 1, and the results were shown in FIG. 2; it can be seen from FIG. 2 that the gellant self-assembles into a three-dimensional network structure, thereby stabilizing the fuel molecules to form a gel.

Figure 3:
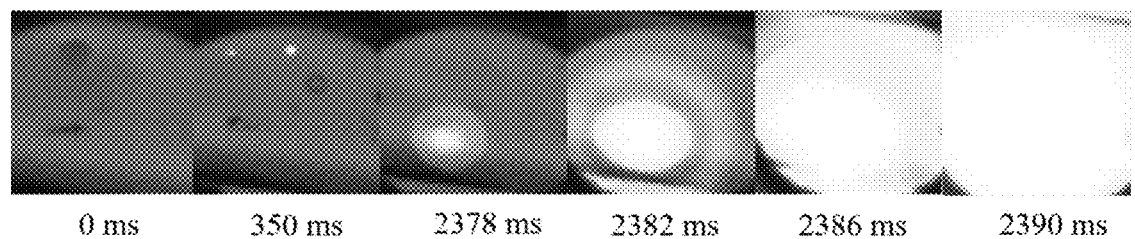
FIG. 3 shows a graph of a droplet ignition experiment of the JP-10 gelled fuel prepared in Use Example 1.

3) An ignition experiment was conducted on the gelled fuel prepared in Use Example 1, and photos at different times were shown in FIG. 3; it can be seen from FIG. 3 that the gelled fuel has a shorter ignition delay time of 2378 ms and a higher combustion rate.

Figure 4:
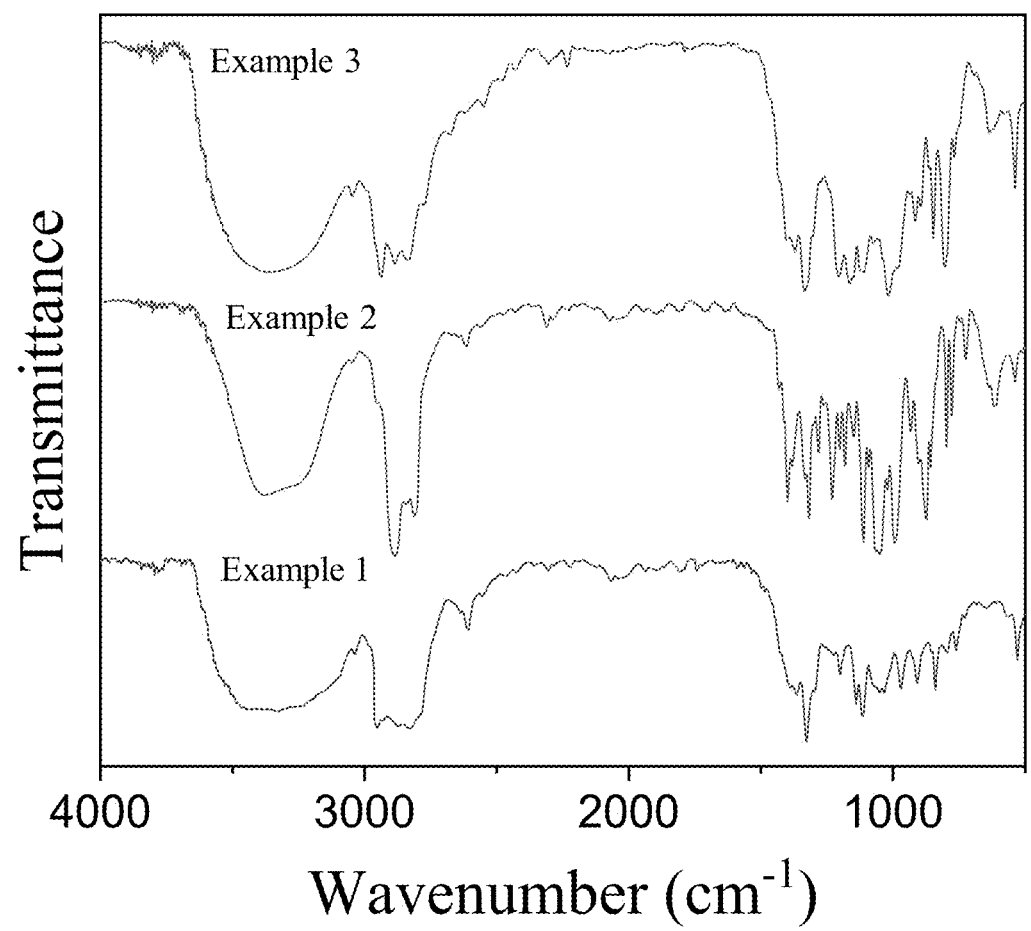
FIG. 4 shows infrared spectrograms of low-molecular mass organic gellants prepared in Examples 1 to 3.

4) Fourier transform infrared spectroscopy was conducted on the low-molecular mass organic gellants prepared in Example 1, Example 2 and Example 3, and the results were shown in FIG. 4. It can be seen from FIG. 4 that a stretching vibration peak corresponding to a hydroxyl group in mannitol is around 3385 cm$^{-1}$; 3040 cm$^{-1}$ is carbon stretching vibration of C—H of the cyclopropane structure; peaks of Examples 1 to 3 at 2800 cm$^{-1}$ to 2950 cm$^{-1}$ are C—H stretching vibration peaks of an alkyl group, and their differences represent a difference in the structures of the low-molecular mass organic gellants prepared in Examples 1 to 3; and stretching vibrations of ether bonds appear around 1200 cm$^{-1}$ and 1111 cm$^{-1}$. Infrared spectrum test shows that the low-molecular mass organic gellants prepared in Examples 1 to 3 each have cyclopropane and ether bonds in their structure, indicating that the cyclopropane structure is successfully introduced into the mannitol.

The above descriptions are merely exemplary implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A low-molecular mass organic gelling compound, having a structure selected from the following:

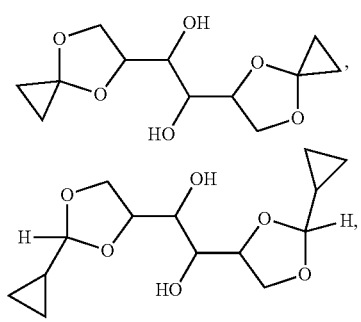

-continued

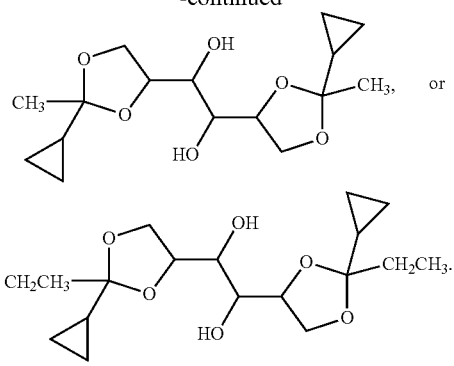

2. A preparation method for a low-molecular mass organic gelling compound as recited in claim 1, comprising:
mixing D-mannitol, a high-tension structure-containing compound, a catalyst, and an organic solvent to conduct condensation to obtain the low-molecular mass organic gelling compound; wherein
the high-tension structure-containing compound is selected from the group consisting of cycloacetone, cyclopropanecarboxaldehyde, cyclopropyl methyl ketone, and cyclopropyl ethyl ketone; and
the catalyst is selected from the group consisting of zinc chloride and p-toluenesulfonic acid.

3. The preparation method of claim 2, wherein the D-mannitol and the high tension structure-containing compound have a molar ratio of 1:(2.0-3.5).

4. The preparation method of claim 2, wherein the zinc chloride and the D-mannitol are present in a molar ratio of (0.03-0.06):0.05; and the p-toluenesulfonic acid and the D-mannitol are present in a molar ratio of (0.01-0.03):0.05.

5. The preparation method of claim 2, wherein the condensation is conducted at 20° C. to 60° C. for 12 h to 48 h.

6. The preparation method of claim 2, wherein the organic solvent is selected from the group consisting of dimethylformamide and 1,2-dimethoxyethane.

* * * * *